United States Patent [19]

Snow et al.

[11] 4,228,351
[45] Oct. 14, 1980

[54] METHOD FOR MEASURING THE DENSITY OF LIGHTWEIGHT MATERIALS

[75] Inventors: Samuel G. Snow, Oak Ridge; Edward J. Giacomelli, Knoxville, both of Tenn.

[73] Assignee: The United States of America as represented by the United States Department of Energy, Washington, D.C.

[21] Appl. No.: 15,259

[22] Filed: Feb. 26, 1979

[51] Int. Cl.² .................. G01N 23/20; G21K 1/00
[52] U.S. Cl. ............................... 250/273; 250/272
[58] Field of Search ........... 250/272, 273, 274, 277 R, 250/278, 279, 359, 360

[56] References Cited

U.S. PATENT DOCUMENTS

| 4,123,654 | 10/1978 | Reiss | 250/273 |
| 4,147,931 | 4/1979 | Puumalainen | 250/273 |

Primary Examiner—Alfred E. Smith
Assistant Examiner—Thomas P. O'Hare
Attorney, Agent, or Firm—Richard G. Besha; Stephen D. Hamel; Louis M. Deckelmann

[57] ABSTRACT

This invention relates to a nondestructive method for measuring the density of articles composed of elements having a low atomic number such as plastic and carbon composites. The measurement is accomplished by striking the article with a collimated beam of X radiation, simultaneously monitoring the radiation scattered and the radiation transmitted by the article, then relating the ratio of the radiation scattered to the radiation transmitted with the density of the article. The above method is insensitive to all variables except density.

2 Claims, 4 Drawing Figures

METHOD FOR MEASURING THE DENSITY OF LIGHTWEIGHT MATERIALS

BACKGROUND OF THE INVENTION

This invention was made in the course of, or under, a contract with the U.S. Department of Energy.

Conventional nondestructive techniques for measuring density are dependent upon the thickness of the article. Frequently, accurate thickness measurements are difficult to obtain for articles having a variable and complex geometry. Consequently, the inaccurate thickness measurement is responsible for poor precision in density measurements.

In the prior art, the fundamental law governing the attenuation of penetrating radiation is utilized for determining the density of materials. Consequently, the use of penetrating radiation is dependent upon differential absorption. It has been determined by experimentation that a beam of penetrating radiation with an intensity of I passing through a thickness of material $\Delta x$ undergoes a decrease in intensity of $\Delta I$. The decrease in intensity has been found to be proportional to the intensity of the incident beam and the thickness of the absorber. In mathematical form, the decrease in intensity is stated as: $\Delta I = -\mu I \Delta x$, where $\mu$ is a constant of proportionality and the negative sign indicates a decrease in intensity. This equation can be written in differential form and then integrated to provide:

$dI = -I\mu dx$; $I = I_o \exp(-\mu x)$; where
$I_o$ = intensity of incident radiation;
$I$ = intensity of transmitted radiation;
$x$ = thickness of specimen; and
$\mu$ = linear absorption coefficient of material.

The mass of absorption coefficient $\mu_m$ is substituted for the linear absorption coefficient $\mu$ for relating the density of a material to the law governing the absorption of penetrating radiation. The substitution is represented mathematically as follows: $\mu_m = \mu/\rho$, where $\rho$ equals the density of a material. The integrated form with the substitution is as follows: $I = I_o \exp(-\mu_m \rho x)$.

In the conventional methods utilizing a beam of penetrating radiation for measuring the density of a material, the requirement for knowing the thickness of the specimen is evident in the mathematical form of the fundamental law governing the attenuation of a radiation beam. However, a technique for measuring density, independent of the specimen thickness has been presented in the following references: Snow, S. G., "Compton Scattering Technique for Measuring Density," Union Carbide Corporation, Nuclear Division, Report Y-1751, dated Feb. 12, 1971; and S. Bukshpan, Dan Kedem, and Drora Kedem, "Detection of Imperfections by Means of Narrow-Beam Gamma Scattering," Materials Evaluation, Vol. XXXIII, No. 10, published by American Society for Nondestructive Testing, Chicago, Illinois, October, 1975. In these references, the intensity of the radiation scattered by the specimen of material is related to the density of the material without measuring the thickness of the specimen. However, the poor accuracy of the density measurements obtained from the intensity of the scattered radiation is a severe limitation. Also, the scattering technique is limited by the sensitivity of the accuracy to the relative positions of the incident beam, detector and specimen.

Thus, there exists a need for an improved method for measuring the density of material without knowing the specimen thickness that will provide the accuracy required and desired for characterization of lightweight materials such as plastics, paper, and various carbon composites, for example. The present invention was conceived to meet this need in a manner to be described hereinbelow.

SUMMARY OF THE INVENTION

It is the object of the present invention to provide an accurate nondestructive method for measuring the density of lightweight materials without knowledge of the specimen thickness.

The above object has been accomplished in the present invention by providing a method for determining the density of a lightweight material comprising the steps of (a) directing a collimated beam of X radiation onto a specimen of said material at a fixed oblique angle of incidence;

(b) simultaneously measuring the X rays transmitted and scattered by said specimen with a first detector positioned in a plane parallel and in line with the beam of radiation on the side of the specimen opposite the origin of the radiation beam for measuring the transmitted radiation, and with a second detector positioned in a parallel plane at an acute angle from the first detector on the side of the specimen opposite the origin of the radiation beam for measuring the scattered radiation;

(c) recording the value for the X rays transmitted and scattered by the specimen;

(d) computing the ratio of the radiation scattered to the radiation transmitted; and (e) comparing the computed ratio value with ratio values computed from corresponding measurements of standards with known densities that were prepared from similar material for determining the density of the specimen.

DESCRIPTION OF THE PREFERRED EMBODIMENT

Figure 1:
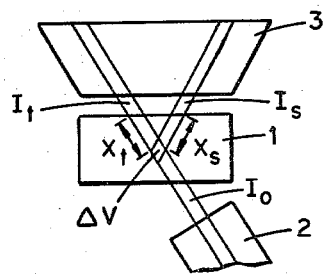
FIG. 1 is a schematic drawing of an arrangement of the equipment required for measuring the density of materials by the present method.

One arrangement of the equipment required in the present invention for measuring the density of lightweight materials is shown in FIG. 1 of the drawings. Penetrating X radiation is utilized for measuring the density of the specimen materials. Independence from the thickness of the material is achieved by simultaneously monitoring the X rays transmitted and scattered by the material.

A highly collimated beam of X rays $I_o$ is directed by means of a collimator 2 into a specimen 1 of lightweight material. The X rays are absorbed and scattered as they pass through the material. Consequently, the X rays are transmitted with a reduced intensity. The amount of absorption and scattering that occurs as the X rays pass through the material is dependent upon several variables including the density of the material. The equipment for the present method has been arranged so that the measurement effected by the method is insensitive to all variables except density. The transmitted X rays $I_t$ and the scattered X rays $I_s$ from the specimen 1 are collimated by a common collimator 3.

The density of a lightweight specimen can be determined by obtaining the ratio of the scattered to transmitted X rays that exit from the specimen. The relationship between the scattered and transmitted X rays and density is presented by the following equation:

$$I_s/I_t = C\rho e^{(\mu_t x_t - \mu_s x_s)},$$

where
$C=(N_A/A)\,d\beta\Delta x\Delta\chi$
$I_s$ is the scattered X-ray intensity
$I_t$ is the transmitted X-ray intensity
$\rho$ is the density of scattering volume, $\Delta v$, in the sample material
$\mu_s$ is the linear attenuation coefficient for scattered X rays
$\mu_t$ is the linear attenuation coefficient for transmitted X rays
$x_s$ is the path length of scattered X rays from scattering volume $\Delta v$ to surface of the specimen
$x_t$ is the path length of the transmitted X rays from scattering volume $\Delta v$ to surface of the specimen
$N_A$ is Avogadro's number
$A$ is the atomic weight of specimen
$d\beta$ is the differential scattering cross section
$\Delta x$ is the thickness of scattering volume in the transmitted X-ray direction
$\Delta\chi$ is the solid angle subtended by window of scattered X-ray collimator The linear attenuation coefficient for scattered X rays ($\mu_s$) is approximately equal to the linear attenuation coefficient for transmitted X rays ($\mu_t$). Then, the sample (specimen) of lightweight material can be positioned so that the scattered X-ray path length ($x_s$) is equal to the transmitted X-ray path length ($x_t$). Now, it can be shown that the ratio of $I_s$ to $I_t$ is equal to the density ($\rho$) of the scattering volume times a constant (C) which is found experimentally by using standards of the lightweight material having known densities. The above statements are represented by the following equations: $\mu_s \approx \mu_t$, and positioning the sample so that $x_s=x_t$, then $I_s/I_t=C\rho$. *The density ($\rho$) of the scattering volume can be found directly and is independent of the thickness of the sample material.*

Figure 3:
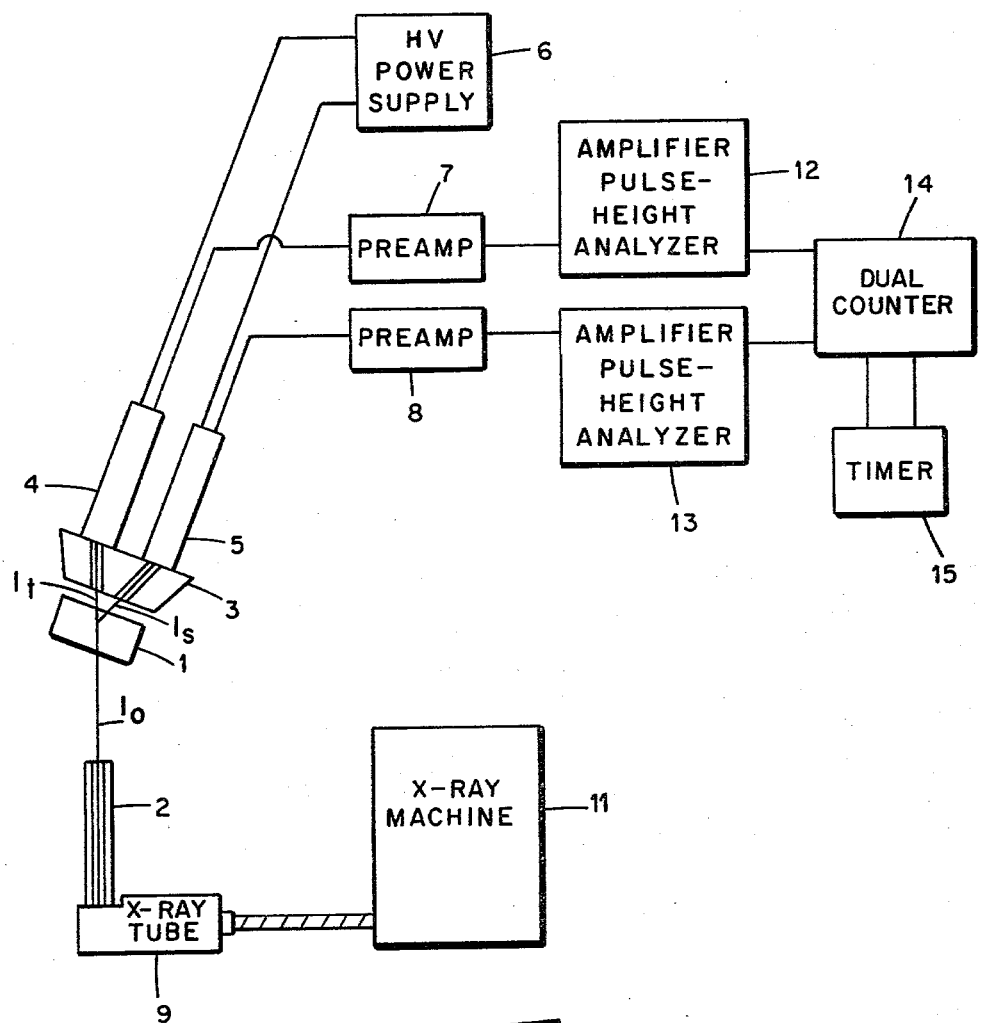
FIG. 3 is a block diagram of the instrumentation utilized for testing the present method.

A block diagram of the instrumentation used for testing the present method is illustrated in FIG. 3 of the drawings. The X-ray source 11 is a GE 75-kV X-ray machine with a GE EA-75 X-ray tube 9 which has a tungsten target and a beryllium window. The scattered and transmitted X-ray intensities ($I_S$ and $I_t$) are measured with two standard scintillation type detectors. The incident-beam collimator 2 is coupled to the X-ray tube 9 and directs a collimated beam $I_o$ into the sample 1. The transmitted beam, $I_t$, and the scattered beam $I_S$, from the sample 1 are collimated by the collimator 3. The transmitted beam is detected by a detector 4 and the scattered beam is detected by a detector 5. Each of the detectors 4 and 5 is a sodium iodide (tellurium) crystal optically coupled to a respective photomultiplier tube, for example. A high voltage power supply 6 is coupled to each of the detectors 4 and 5.

The output of the detector 4 is coupled to a preamplifier 7 which in turn is coupled to an amplifier pulse-height analyzer unit 12. The output of the detector 5 is coupled to a preamplifier 8 which in turn is coupled to an amplifier pulse-height analyzer unit 13. The outputs of the units 12 and 13 are coupled to a dual counter (scaler) 14 which in turn is coupled to a timer 15.

The projection of the collimated, transmitted and scattered beams form a 45-degree angle and intersect (defining the scattering volume $\Delta v$, see FIG. 1) at three centimeters below the bottom surface of the collimator assembly 3.

Figure 2:
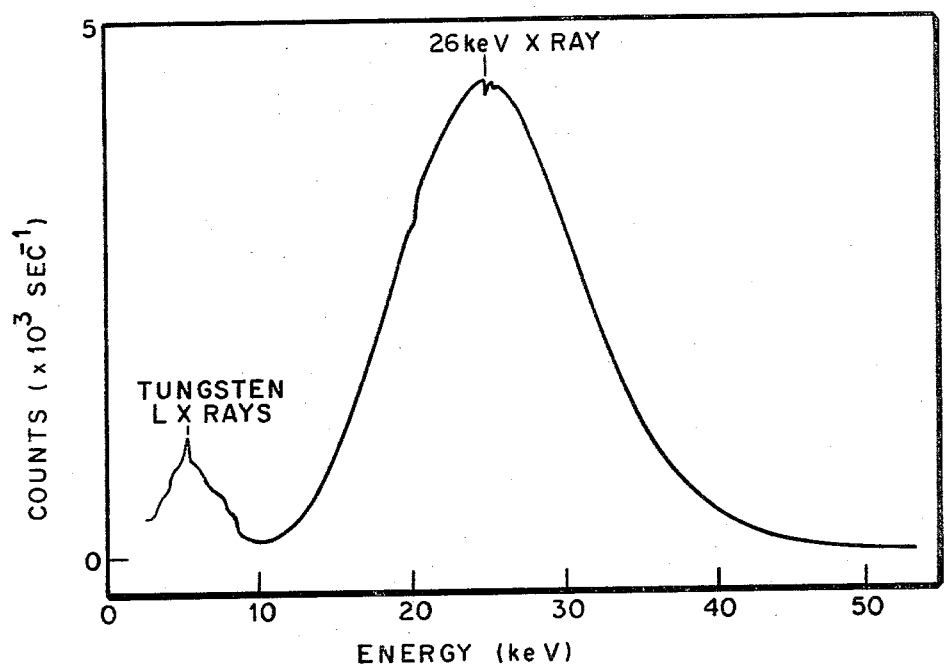
FIG. 2 is a plot illustrating the spectrum of the incident X-ray beam obtained in a test of the present method.

The bremsstrahlung radiation produced in an X-ray tube has a broad energy distribution. In order to narrow this distribution and form a peak-shaped incident beam spectrum, it is necessary to filter the incident beam. A tin/nickel combination is used for this filter. This combination was chosen because L X rays from the tungsten target were interfering with the measurement. The tin filter shapes a 26-keV X-ray peak, and the nickel filter separates that peak from the tungsten L X-ray peak. FIG. 2 shows the resulting spectra (for the X-ray machine operating settings of 40 kV and 70 mA). Pulse-height discrimination is then used to select only X rays from the 26-keV peak for counting.

The method of utilizing the present invention is set forth in the above Summary of the Invention to which reference is made.

Figure 4:
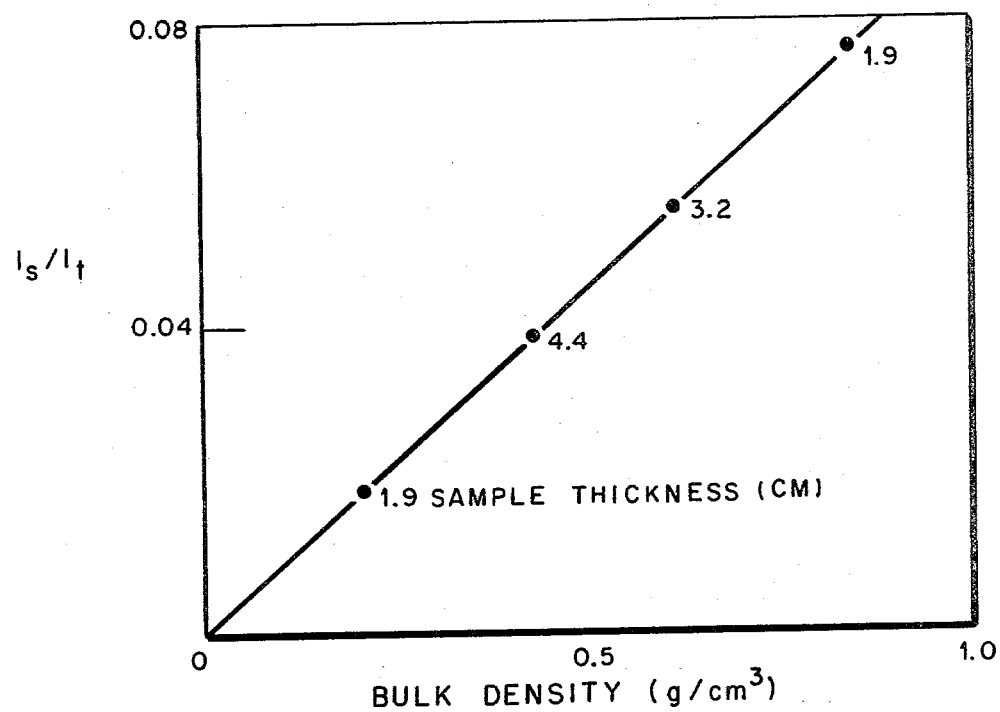
FIG. 4 is a graph showing the linear relationship between the ratio of the scattered to the transmitted X rays and the density of pressed carbon specimens used in a test of the present method.

Samples of pressed carbon materials were used to evaluate the present measurement method. The densities of 4 different pressed carbon composites were measured for comparison with the conventional method of measuring bulk densities. The dimensions of the specimens were: a width of 4.44 cm, a length of 6.35 cm, and thicknesses of 1.9 cm, 3.2 cm, and 4.4 cm. Density measurements by the conventional method indicated that the densities of the specimens ranged from 0.21 to 0.86 gm/cc. The measurements made with the present invention on the specimens with known densities were taken at the same measurement depth (depth of $\Delta v$) in each specimen. The X rays from the incident beam that were scattered and transmitted by the specimens were monitored simultaneously for a 1000-second count time. The ratios of the intensity of the scattered to the transmitted X rays ($I_s/I_t$) were then plotted against the known densities of the specimens. The resulting linear relationship between the ratio of the intensities of scattered to the transmitted X rays and the density of the specimens is illustrated in FIG. 4 of the drawings. Next to each data point on the graph is the specimen thickness in centimeters, demonstrating that not only is the relationship between measured ratio and density a linear fit, but is also independent of specimen thickness. The maximum deviation from the fit in FIG. 4 was 0.8% with a correlation coefficient of 0.9998. (A value of 0 means that no correlation exists and a value of 1 represents a perfect fit.) The measurement precision, based on counting statistics for a 1000-second count time, was better than 0.5%.

This invention has been described by way of illustration rather than by limitation and it should be apparent that it is equally applicable in fields other than those described.

What is claimed is:

1. A method for determining the density of lightweight materials having low atomic numbers including plastics and carbon composites comprising the steps of:

directing a collimated beam of X-radiation onto a sample of lightweight material at a fixed oblique angle of incidence such that the scattered X-ray path length is equal to the transmitted X-ray path length within said sample;

simultaneously measuring the X rays transmitted and scattered by said sample with a first detector for measuring the transmitted radiation positioned in alignment with said beam of X radiation on that side of said sample opposite the origin of said beam and with a second detector for measuring scattered radiation positioned at an acute angle with respect to the first detector on that side of said sample opposite the origin of the radiation beam;

determining the ratio of the radiation scattered to the radiation transmitted; and comparing said ratio with ratio values determined from corresponding measurements of standards having known densities that were prepared from similar material for determining the density of said sample material independent of the thickness thereof.

2. The method set forth in claim 1, wherein said acute angle is 45°, and further including the step of collimating said transmitted and scattered radiation prior to said measurement step.

* * * * *